United States Patent
Riggs et al.

(10) Patent No.: US 9,220,719 B2
(45) Date of Patent: Dec. 29, 2015

(54) SINGLE DOSE ORAL FORMULATIONS AND METHODS FOR TREATMENT OF CATS WITH ECTOPARASITICIDAL SPINOSAD

(71) Applicant: Eli Lilly and Company, Indianapolis, IN (US)

(72) Inventors: Kari Lynette Riggs, Greenfield, IN (US); Daniel Earl Snyder, Indianapolis, IN (US); Michelle Leigh Totten, Fishers, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 0 days.

(21) Appl. No.: 13/944,904

(22) Filed: Jul. 18, 2013

(65) Prior Publication Data

US 2014/0031306 A1 Jan. 30, 2014

Related U.S. Application Data

(60) Provisional application No. 61/676,023, filed on Jul. 26, 2012.

(51) Int. Cl.
| | |
|---|---|
| *A61K 31/70* | (2006.01) |
| *A61K 31/7048* | (2006.01) |
| *A01N 43/22* | (2006.01) |
| *A61K 9/00* | (2006.01) |
| *A61K 9/20* | (2006.01) |

(52) U.S. Cl.
CPC ............ *A61K 31/7048* (2013.01); *A01N 43/22* (2013.01); *A61K 9/0056* (2013.01); *A61K 9/2054* (2013.01)

(58) Field of Classification Search
CPC .. A61K 31/7048; A61K 9/2054; A01N 43/22
See application file for complete search history.

(56) References Cited

U.S. PATENT DOCUMENTS

| | | | |
|---|---|---|---|
| 6,664,237 | B1 | 12/2003 | Snyder |
| 2007/0149464 | A1* | 6/2007 | Billen et al. .................... 514/28 |

FOREIGN PATENT DOCUMENTS

| | | |
|---|---|---|
| EP | 2248422 A1 | 11/2010 |
| WO | 01/11963 A1 | 2/2001 |
| WO | 2012/006187 A1 | 5/2012 |

OTHER PUBLICATIONS

Bevier-Tournay, D. E., "Flea and Flea Control" Curr. Vet. Therapy 10: 586-592 (1989).
Conniff, R., "When It Comes to Pesky Flea, Ignorance is Bliss," Smithsonian: 26: 76-85 (1995).
Handbook of Pharmaceutical Salts: Properties, Selection and Use, P. H. Stahl and C. G. Wermuth (Eds.), Wiley-VCH, New York, 2002.
Rust, N. K., and M. W. Dryden, Ann. Rev. Entomol. 42: 451-473 (1997).
Snyder, et al., "Preliminary study on the effectiveness of the novel pulicide, spinosad, for the treatment and control of fleas", Veterinary Parasitology, 150 (2007) 345-351.

* cited by examiner

*Primary Examiner* — Elli Peselev
(74) *Attorney, Agent, or Firm* — McAndrews Held & Malloy, Ltd.

(57) ABSTRACT

This invention provides a single-dose oral formulation of spinosad for the extended control of a *C. felis* infestation on a cat at a predictable dose of spinosad that is suitable for administration once every 30 days (i.e., one month). The invention also provides methods of using the formulation of spinosad.

34 Claims, No Drawings

SINGLE DOSE ORAL FORMULATIONS AND METHODS FOR TREATMENT OF CATS WITH ECTOPARASITICIDAL SPINOSAD

Among the most common ectoparasites of cats world-wide are cat fleas, *Ctenocephalides felis*, also referred to as *C. felis*. Fleas may annoy both the animal it infests and the owner of the companion animal. Frequently, fleas cause more serious problems by inducing flea-allergy dermatitis. It has been estimated that flea-related diseases account for over 50% of the dermatological cases reported to veterinarians [D. E. Bevier-Tournay, "Flea and Flea Control" Curr. Vet. Therapy 10: 586-592 (1989)]. In addition, the cat flea is known to transmit tapeworms in cats and dogs and has been implicated in the transmission of cat scratch disease and murine typhus. Furthermore, economic expenses involved in flea control are high. In the United States, for example, pet owners spend over $1 billion dollars for flea control products annually [R. Conniff, "When It Comes to Pesky Flea, Ignorance is Bliss," Smithsonian: 26: 76-85 (1995)].

Treatments currently available achieve varying degrees of success. Most treatments involve chemicals applied to indoor and outdoor surfaces, as well as to the pet. The chemicals used include a variety of carbamates, organophosphates, pyrethrins and pyrethroids. These compounds often have toxic side effects can be a problem for both the pet and its owner. For example, concentrated forms of pyrethroids available are lethal to cats and, thus, cannot and should not be used on cats. In addition, there is evidence that the use of these chemicals has led to multiple examples of insecticide resistance [N. K. Rust and M. W. Dryden, Ann. Rev. Entomol. 42: 451-473 (1997)].

The spinosyns (also known as A83453 factors) are agricultural insecticides that have shown activity against southern armyworm and other insects in the order Lepidoptera, and cotton aphid and other members of the order Homoptera. Spinosyns are naturally derived fermentation productsthat are produced by cultivation of *Saccharopolyspora spinosa*. The fermentation produces many factors, including spinosyn A and spinosyn D (also called A83543A and A8354D). Spinosyn A and spinosyn D are the two spinosyns that are most active as insecticides. A product comprised mainly of these two spinosyns is available commercially under the common name "spinosad" (see, e.g., U.S. Pat. No. 6,664,237), and is also sold in the United States under the name of Comfortis® which is the first FDA-approved, chewable, beef-flavored tablet that kills fleas and prevents flea infestations on dogs for a full month.

In addition, the long-term effectiveness of treatments is of great concern to pet owners. In this regard, a treatment to control *C. felis* infestation on cats that can be conveniently given to the cat at a minimal dosing frequency but that is effective for an extended period of time is highly desirable. Ideally, such a treatment would provide prolonged residual control of a *C. felis* infestation on a cat following administration of a single dose of treatment.

Therefore, there exists a need for extended control of a *C. felis* infestation on a cat utilizing a predictable dose schedule of an ectoparasicidal compound. Accordingly, the present invention provides a single-dose oral formulation of spinosad which exhibits desirable properties and provides related advantages as well.

This invention provides a single-dose oral formulation of spinosad for the extended control of a *C. felis* infestation on a cat at a predictable dose of spinosad that is suitable for administration once every 30 days (i.e., one month). The invention also provides methods of using the formulation of spinosad.

The present invention provides a single dose of spinosad for controlling a *C. felis* infestation on a cat that is unexpected in light of comparison studies with other animal species. The present invention provides greater residual efficacy in cats at a longer post-administration duration, (e.g., 35 days or 37 days) after the single dose of spinosad is administered. The present invention may be orally administered to a cat once per month and maintain systemic efficacy for the entirety of the treatment period. The present invention may be orally administered as a tablet at a single dosage, including as a chewable tablet, and may advantageously be administered with or without food.

One aspect of the present invention provides a single-dose oral formulation for controlling a *C. felis* infestation on a cat. The formulation comprises an ectoparasiticidal amount of spinosad, microcrystalline cellulose, hydroxypropylcellulose, colloidal silicon (anhydrous), croscarmellose sodium, and magnesium stearate wherein the formulation is a tablet or capsule suitable for administration once every 30 days at a dose of at least about 50 milligrams (mg) of spinosad per kilogram (kg) of body weight of the cat. In some embodiments, the formulation further comprises an artificial beef flavor.

Spinosad can react to form physiologically acceptable derivatives or salts that are also useful in the methods and formulations of this invention. The salts can be prepared using standard procedures for salt preparation. The term "pharmaceutically acceptable salt" refers to an addition salt that exists in conjunction with the acidic or basic portion of spinosad. Such salts include the pharmaceutically acceptable salts listed in HANDBOOK OF PHARMACEUTICAL SALTS: PROPERTIES, SELECTION AND USE, P. H. Stahl and C. G. Wermuth (Eds.), Wiley-VCH, New York, 2002 which are known to the skilled artisan. Pharmaceutically acceptable salts of an acid addition nature are formed when spinosad and any of its intermediates containing a basic functionality are reacted with a pharmaceutically acceptable acid. Pharmaceutically acceptable acids commonly employed to form such acid addition salts include inorganic and organic acids. Pharmaceutically acceptable salts of a base addition nature are formed when spinosad and any of its intermediates containing an acidic functionality are reacted with a pharmaceutically acceptable base. Pharmaceutically acceptable bases commonly employed to form base addition salts include organic and inorganic bases.

For example, spinosyn A can be neutralized with an appropriate acid to form an acid addition salt. The acid addition salts include salts formed by reaction with either an organic or inorganic acid such as, for example, sulfuric, hydrochloric, phosphoric, acetic, succinic, citric, lactic, maleic, fumaric, cholic, pamoic, mucic, glutamic, camphoric, glutaric, glycolic, phthalic, tartaric, formic, lauric, stearic, salicylic, methanesufonic, benzenesulfonic, sorbic, picric, benzoic, cinnamic, and like acids.

In addition to pharmaceutically acceptable salts, other salts are included in the present invention. They may serve as intermediates in the purification of compounds or in the preparation of other pharmaceutically-acceptable salts, or are useful for identification, characterization or purification.

Spinosad is a natural product composed of spinosyn factors A and D, in normally a 17:3 ratio, the structures of which are:

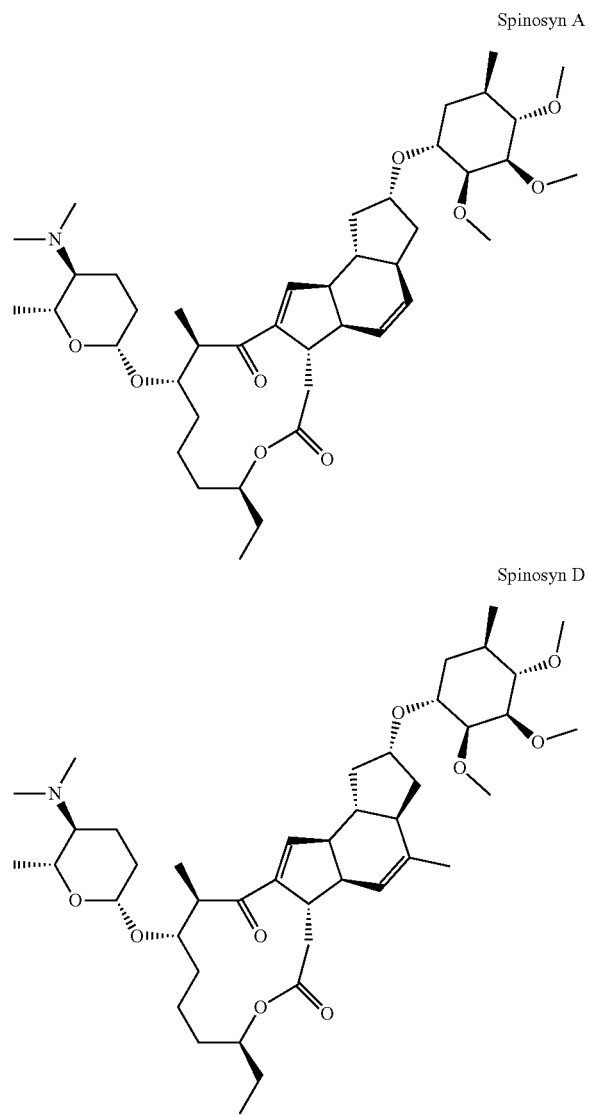

Systemic efficacy (ingestion of blood containing spinosad by the blood feeding parasites, such as fleas) provides different mode of exposure compared to topically applied ectoparasiticides where contact with the parasite at the skin surface is the mode of exposure. The advantages of oral systemic treatments and killing of parasites from ingestion of blood, compared to topical applications and contact killing, include: a) reduced exposure to the human applicator and children and objects in the animal's environment (e.g., flooring, carpets, furniture); b) no worry about loss from exposure of the animal to water (lakes, streams, bathing, etc.) or from loss due to rubbing; c) no concern about UV exposure and degradation; d) no problems with oxidation from oils on skin, etc.; and e) assurance that the entire dose is administered (compared to a topical application where some of the dose may drip off, rub off and/or remain in the dispensing tube immediately after treatment).

The formulations of this invention may further include, in combination with the spinosyn component, one or more other active compounds, including those that have activity against the C. felis to be controlled, such as, for example, synthetic pyrethroids, natural pyrethins, organophosphates, organochlorines, carbamates, foramidines, avermectins, milbemycins, insect growth regulators (including chitin synthesis inhibitors, juvenile hormone analogs, and juvenile hormones), nitromethylenes, pyridines and pyrazoles.

All ratios, percentages, and parts discussed herein are "by weight" unless otherwise specified.

The term "oral formulation" means that spinosad, either alone or in combination with one or more of the other types of compounds listed supra, is formulated into a product or formulation suitable for administering to the animal by mouth. These products or formulations include, but are not limited to, tablets, capsules, liquids, gels, pastes, oral sprays, buccal formulations, powders and chewable treats or animal feeds containing the active component or components. Generally, such formulations include a physiologically acceptable carrier. Such carriers are well known in the veterinary arts. Animal feeds are particularly useful carriers.

The term "controlling a C. felis infestation" refers to prevention of C. felis infestations, treatment of C. felis infestations, or prevention and treatment of C. felis infestations. Furthermore, "controlling a C. felis infestation" includes preventing, minimizing or eliminating an infestation by C. felis. In some embodiments, the C. felis presents at a stage selected from the group consisting of egg, larvae, and adult.

The term "single-dose formulation" means that one dose of the formulation effectively controls the C. felis infestation for a prolonged time. The term "prolonged time" comprises a period of at least 30 days. The term "long-acting" means that the activity lasts for a prolonged time, for example a period of 35 days or 37 days. "Suitable for oral administration once every 30 days" means an oral administration which provides the requisite period of protection (at least about every 30 days) while maintaining the requisite efficacy, as defined below.

The formulations of the present invention may advantageously provide long-acting control (e.g., residual efficacy) of a C. felis infestation in cats. In some embodiments, the formulation has greater than 75% residual efficacy at 30 days post-administration. In other embodiments, the formulation has greater than 90% residual efficacy at 30 days post-administration. In yet other embodiments, the formulation has greater than 95% residual efficacy at 30 days post-administration. In some embodiments, the formulation has greater than 75% residual efficacy at 35 days post-administration. In other embodiments, the formulation has greater than 90% residual efficacy at 35 days post-administration. In some embodiments, the formulation has greater than 75% residual efficacy at 37 days post-administration. In other embodiments, the formulation has greater than 90% residual efficacy at 37 days post-administration.

The formulations of the present invention comprise an effective amount of spinosad administered orally to the cat. The terms "effective amount" and "ectoparasiticidal amount" refer to the amount needed to control the C. felis infestation. As those in the art will understand, this amount will vary depending upon a number of factors. These factors include, for example, the breed of cat being treated, its weight, and general physical condition.

In general, an effective amount refers to a dose of at least about 50 mg of spinosad per kg of body weight of the cat. The term "about 50 mg of spinosad" refers to a dose of spinosad well known to a person of ordinary skill in the art. As such, a person of ordinary skill in the art would understand the range of doses encompassed by the term "about 50 mg of spinosad." For example, a dose of 49.8 mg to 50.2 mg of spinosad is "about 50 mg of spinosad."

In one embodiment, the dose is at least about 50 mg to about 100 mg of spinosad per kg of body weight of the cat. In another embodiment, the dose is at least about 75 mg of spinosad per kg of body weight of the cat. The term "about 75 mg of spinosad" refers to a dose of spinosad well known to a person of ordinary skill in the art. As such, a person of ordinary skill in the art would understand the range of doses encompassed by the term "about 75 mg of spinosad." In yet another embodiment, the dose is at least about 100 mg of spinosad per kg of body weight of the cat. The term "about 100 mg of spinosad" refers to a dose of spinosad well known to a person of ordinary skill in the art. As such, a person of ordinary skill in the art would understand the range of doses encompassed by the term "about 100 mg of spinosad." For example, a dose of 94.4 mg to 102.9 mg, or 98.9 mg to 102.9 mg, of spinosad is "about 100 mg of spinosad."

An example dosing schedule according to the present invention is found in Table 1.

TABLE 1

Example Dosing Schedule of Spinosad

| Cat Body Weight per lb (per kg) | Amount of Spinosad per Dose (mg) | Milligrams of Spinosad per lb (per kg) |
|---|---|---|
| 2 to 3 lbs (0.91 to 1.36 kg) | 90 | 30 to 45 mg/lb (66.2 to 98.9 mg/kg) |
| 3.1 to 6.2 lbs (1.41 to 2.81 kg) | 140 | 22.58 to 45.16 mg/lb (49.8 to 99.2 mg/kg) |
| 6.3 to 11.9 lbs (2.86 to 5.40 kg) | 270 | 22.69 to 42.86 mg/lb (50.0 to 94.4 mg/kg) |
| 12 to 24.6 lbs (5.44 to 11.16 kg) | 560 | 22.76 to 46.67 mg/lb (50.2 to 102.9 mg/kg) |

In some embodiments of the present invention, the formulation comprises components at specific weight/weight percentages. For example, in one embodiment, the formulation comprises the following weight/weight percentages:

| | | |
|---|---|---|
| Pharmaceutical grade spinosad (API) | 52.0-54.7% | 53.33% |
| Microcrystalline cellulose, NF/Ph. Eur. | 13.8-14.5% | 14.17% |
| Hydroxypropyl cellulose, NF/Ph. Eur. | 4.9-5.1% | 5.0% |
| Croscarmellose sodium, NF/Ph. Eur. | 5.9-6.2% | 6.0% |
| Colloidal silicon dioxide, NF/Ph. Eur. | 0.49-0.51% | 0.5% |
| Magnesium stearate, NF/Ph. Eur. (non-bovine) | 0.98-1.03% | 1.0% |
| Purified Water, USP/Ph. Eur | | q.s. |

The amount of pharmaceutical grade spinosad Active Pharmaceutical Ingredient (API) may be adjusted to take into account varying potency of spinosyn Factors A+D.

Accordingly, the amount of microcrystalline cellulose may be adjusted to compensate for a potential change in the weight of spinosad. The amount pharmaceutical grade spinosad API listed above assumes 100% potency of spinosyn Factors A+D. Furthermore, the purified water (USP/Ph.Eur.) is used in the manufacturing process of the formulation, but it is evaporated during processing of the formulation. Thus, the amount of purified water is based on the intragranular components of the formulation and may vary to achieve suitable granulation of the formulation.

In another embodiment, the formulation comprises the following weight/weight percentages:

| | | |
|---|---|---|
| Pharmaceutical grade spinosad (API) | 52.0-54.7% | 53.33% |
| Artificial powdered beef flavor PC-0125 (gamma irradiated) | 19.5-20.5% | 20.00% |
| Microcrystalline cellulose, NF/Ph. Eur. | 13.8-14.5% | 14.17% |
| Hydroxypropyl cellulose, NF/Ph. Eur. | 4.9-5.1% | 5.0% |
| Croscarmellose sodium, NF/Ph. Eur. | 5.9-6.2% | 6.0% |
| Colloidal silicon dioxide, NF/Ph. Eur. | 0.49-0.51% | 0.5% |
| Magnesium stearate, NF/Ph. Eur. (non-bovine) | 0.98-1.03% | 1.0% |
| Purified Water, USP/Ph. Eur | | q.s. |

According to the present invention, the term "cat" refers to all members of the *Felis catus* species. In some embodiments, the cat is a kitten.

In some embodiments of the present invention, the formulation is a tablet. Conventional oral tablets generally consist of spinosad, a diluent to assist in increasing the powder mass to a convenient size and improve compressibility, a binder to hold the compressed powder together and a lubricant to assist in densification and ejection from the tablet die. They may also contain a disintegrate to improve disintegration and dissolution as well as stabilizers, colors and flavors. Tablets are often coated to improve appearance or taste or to alter the dissolution properties. Tablets can be designed to dissolve fast or slow, and depending on the actual volume and compressibility of the drug, large or small. Tablets can be made to be chewable or to dissolve under the tongue or in the pouch of the cheek. In some embodiments, the tablet is a chewable tablet. In other embodiments of the present invention, the formulation is a capsule.

In some embodiments of the present invention, the formulation further comprises one or more excipients. In one embodiment, the one or more excipients is selected from the group consisting of microcrystalline cellulose, artificial beef flavor, hydroxypropylcellulose, colloidal silicon (anhydrous), croscarmellose sodium, and magnesium stearate. In another embodiment, the formulation further comprises microcrystalline cellulose, hydroxypropylcellulose, colloidal silicon (anhydrous), croscarmellose sodium, and magnesium stearate. In yet another embodiment, the formulation further comprises microcrystalline cellulose, artificial beef flavor, hydroxypropylcellulose, colloidal silicon (anhydrous), croscarmellose sodium, and magnesium stearate.

Another aspect of the present invention provides a method of treating a *C. felis* infestation on a cat. The method comprises orally administering a single-dose oral formulation comprising an ectoparasiticidal amount of spinosad, microcrystalline cellulose, hydroxypropylcellulose, colloidal silicon (anhydrous), croscarmellose sodium, and magnesium stearate, wherein the formulation is a tablet or capsule suitable for administration once every 30 days at a dose of at least about 50 mg of spinosad per kg of body weight of the cat. The embodiments described above with respect to the single-dose oral formulation are also applicable to the methods of the present invention.

Another aspect of the present invention provides a single-dose oral tablet for controlling a *C. felis* infestation on a cat. In one embodiment, the tablet comprises spinosad, microcrystalline cellulose, artificial beef flavor, hydroxypropylcellulose, colloidal silicon (anhydrous), croscarmellose sodium, and magnesium stearate, wherein the spinosad is present at a dose of 90 mg, and wherein the tablet is suitable for administration once every 30 days. In some embodiments, the tablet comprises the components at the following amounts:

| | |
|---|---:|
| Pharmaceutical grade spinosad (API) | 90 mg |
| Artificial powdered beef flavor PC-0125 (gamma irradiated) | 33.75 mg |
| Microcrystalline cellulose, NF/Ph. Eur. | 23.91 mg |
| Hydroxypropyl cellulose, NF/Ph. Eur. | 8.44 mg |
| Croscarmellose sodium, NF/Ph. Eur. | 10.13 mg |
| Colloidal silicon dioxide, NF/Ph. Eur. | 0.84 mg |
| Magnesium stearate, NF/Ph. Eur. (non-bovine) | 1.69 mg |
| Purified Water, USP/Ph. Eur | q.s. |

In another embodiment, the tablet comprises spinosad, microcrystalline cellulose, artificial beef flavor, hydroxypropylcellulose, colloidal silicon (anhydrous), croscarmellose sodium, and magnesium stearate, wherein the spinosad is present at a dose of 140 mg, and wherein the tablet is suitable for administration once every 30 days. In some embodiments, the tablet comprises the components at the following amounts:

| | |
|---|---:|
| Pharmaceutical grade spinosad (API) | 140 mg |
| Artificial powdered beef flavor PC-0125 (gamma irradiated) | 52.50 mg |
| Microcrystalline cellulose, NF/Ph. Eur. | 37.20 mg |
| Hydroxypropyl cellulose, NF/Ph. Eur. | 13.13 mg |
| Croscarmellose sodium, NF/Ph. Eur. | 15.75 mg |
| Colloidal silicon dioxide, NF/Ph. Eur. | 1.31 mg |
| Magnesium stearate, NF/Ph. Eur. (non-bovine) | 2.63 mg |
| Purified Water, USP/Ph. Eur | q.s. |

In another embodiment, the tablet comprises spinosad, microcrystalline cellulose, artificial beef flavor, hydroxypropylcellulose, colloidal silicon (anhydrous), croscarmellose sodium, and magnesium stearate, wherein the spinosad is present at a dose of 270 mg, and wherein the tablet is suitable for administration once every 30 days. In some embodiments, the tablet comprises the components at the following amounts:

| | |
|---|---:|
| Pharmaceutical grade spinosad (API) | 270 mg |
| Artificial powdered beef flavor PC-0125 (gamma irradiated) | 101.26 mg |
| Microcrystalline cellulose, NF/Ph. Eur. | 74.74 mg |
| Hydroxypropyl cellulose, NF/Ph. Eur. | 25.31 mg |
| Croscarmellose sodium, NF/Ph. Eur. | 30.38 mg |
| Colloidal silicon dioxide, NF/Ph. Eur. | 2.53 mg |
| Magnesium stearate, NF/Ph. Eur. (non-bovine) | 5.06 mg |
| Purified Water, USP/Ph. Eur | q.s. |

In another embodiment, the tablet comprises spinosad, microcrystalline cellulose, artificial beef flavor, hydroxypropylcellulose, colloidal silicon (anhydrous), croscarmellose sodium, and magnesium stearate, wherein the spinosad is present at a dose of 560 mg, and wherein the tablet is suitable for administration once every 30 days. In some embodiments, the tablet comprises the components at the following amounts:

| | |
|---|---:|
| Pharmaceutical grade spinosad (API) | 560 mg |
| Artificial powdered beef flavor PC-0125 (gamma irradiated) | 210 mg |
| Microcrystalline cellulose, NF/Ph. Eur. | 148.8 mg |
| Hydroxypropyl cellulose, NF/Ph. Eur. | 52.52 mg |
| Croscarmellose sodium, NF/Ph. Eur. | 63 mg |
| Colloidal silicon dioxide, NF/Ph. Eur. | 5.24 mg |
| Magnesium stearate, NF/Ph. Eur. (non-bovine) | 10.52 mg |
| Purified Water, USP/Ph. Eur | q.s. |

The embodiments described above with respect to the single-dose oral formulation, as they apply to a tablet, are also applicable to the single-dose oral tablets of the present invention.

EXAMPLE 1

Dose Determination Effectiveness of Spinosad Administered Orally to Cats with *C. Felis* Infestations The "knockdown" and "residual" effectiveness of spinosad can be evaluated following oral administration at four different single dosages, compared to a non-treated control group, against the adult cat flea (*Ctenocephalides felis*) on experimentally infested cats. A minimum effective oral dose in cats can be evaluated based on knockdown efficacy (i.e., on Day 1 following administration) and on residual efficacy (i.e., on Day 30 following administration) against the cat flea (*Ctenocephalides felis*).

Forty cats can be evaluated in a randomized complete block design with cat gender and pretreatment live flea counts used as blocking factors. Five treatment groups of four female and four male cats per group can be orally dosed on Test Day 0: Group (1) can be administered 0 mg/kg vehicle control (empty gelatin capsule); Group (2) can be administered spinosad in a gelatin capsule at a dose of 35 mg/kg body weight; Group (3) can be administered spinosad in a gelatin capsule at a dose of 40 mg/kg body weight; Group (4) can be administered spinosad in a gelatin capsule at a dose of 45 mg/kg body weight; and Group (5) can be administered spinosad in a gelatin capsule at a dose of 50 mg/kg body weight. All cats can consume canned cat food just prior to dosing to ensure they were in a fed state. Each cat can be infested with approximately 100 newly emerged, unfed adult fleas (*C. felis*), on Test Days −6, −1, 5, 12, 19, 28 and 35. Individual animal flea counts can be performed approximately 48-hours post-infestation using the laboratory's comb counting method on Test Days −4, 1, 7, 14, 21, 30 and 37. The Day −4 pre-treatment live flea counts can be used to allocate animals to the five treatment groups. The Day 1, 7, 14, 21, 30 and 37 flea counts can be used to evaluate the knockdown (Day 1) and residual flea efficacy in each of the treated groups compared to the vehicle (negative) control group.

All four spinosad treated groups demonstrated excellent knockdown (100% at Day 1) and post-treatment residual flea efficacy >90% up to and including Day 21 post-treatment as seen in the following table using geometric means (GM). The 50 mg/kg group had zero fleas at each comb count up through Day 21. At Day 30 post-treatment, only the 50 mg/kg group demonstrated consistently high residual flea efficacy (97.33%) based on GM while two (35 and 45 mg/kg) of the three lower spinosad dosage groups had dropped below 90% efficacy at Day 30 as compared to the vehicle control group. The differences in the treatment groups are shown in Table 2.

TABLE 2

Geometric Mean Percent Reduction (Geometric Mean Counts) of Adult *C. felis* Compared to Untreated Control Group in Cats Treated Orally with Spinosad

| Spinosad, Oral Dose (mg/kg) | Days Post Treatment | | | | | |
|---|---|---|---|---|---|---|
| | 1 | 7 | 14 | 21 | 30 | 37 |
| Vehicle Control | 76.0 (—) | 80.0 (—) | 73.7 (—) | 76.2 (—) | 61.6 (—) | 67.9 (—) |
| 35 | 100.00 (0.0) | 100.00 (0.0) | 99.74 (0.2) | 92.94 (5.4) | 80.80 (11.8) | 52.20 (32.4) |
| 40 | 100.00 (0.0) | 100.00 (0.0) | 100.00 (0.0) | 98.74 (1.0) | 91.59 (5.2) | 72.18 (18.9) |

TABLE 2-continued

Geometric Mean Percent Reduction (Geometric Mean Counts) of Adult C. felis Compared to Untreated Control Group in Cats Treated Orally with Spinosad

| Spinosad, Oral Dose (mg/kg) | Days Post Treatment | | | | | |
|---|---|---|---|---|---|---|
| | 1 | 7 | 14 | 21 | 30 | 37 |
| 45 | 100.00 (0.0) | 99.50 (0.4) | 97.22 (2.0) | 93.98 (4.6) | 80.68 (11.9) | 48.29 (35.1) |
| 50 | 100.00 (0.0) | 100.00 (0.0) | 100.00 (0.0) | 100.00 (0.0) | 97.33 (1.6) | 87.50 (8.5) |

The differences in flea count compared to the control group were statistically significant (p<0.05) for all four of the spinosad treated groups at Days 1, 7, 14 and 21 and for the 40 mg/kg and 50 mg/kg groups on Day 30 using both parametric and non-parametric statistical testing.

The present example demonstrates a single oral dose of spinosad at 50 mg/kg provides excellent knockdown (100%) as well as 30 days of residual effectiveness (97.33%) using a geometric mean count against adult C. felis on experimentally infested cats and demonstrated statistically significant differences at all time points compared to the control group. In addition, at 37 days post-treatment, a single oral dose of spinosad at 50 mg/kg provides residual effectiveness (87.50%) using a geometric mean count against adult C. felis. Spinosad was well tolerated throughout the example.

EXAMPLE 2

Pharmacokinetics and Biosimilarity of Spinosad API (80 mg/Kg) and Spinosad Tablets (80 mg/Kg) Following Oral Administration to Cats The plasma concentrations and resulting pharmacokinetics of spinosad tablets when administered orally to adult cats in the fed or fasted state can be evaluated. Twenty four cats (12 male and 12 female) can be dosed with approximately 80 mg/kg spinosad, as either API in gelatin capsules or as spinosad formulated chewable tablets. Serial blood samples can be collected through 672 hours (28 days) after dose administration. Blood samples can be collected within 10% of nominal time (4 samples at 0.5 hours were collected within 23%). Samples can be immediately mixed by inversion several times and stored on ice until centrifuged. The plasma can be collected, split into two approximately equal aliquots and stored frozen at approximately −70° C. until shipped for analysis, and/or analyzed by a validated LC/MS/MS assay.

The post-treatment plasma concentrations and pharmacokinetic parameters of the major factors of spinosad (spinosyn A and D) were determined Non-compartmental analyses were used to analyze the data for this study to determine the systemic exposure as measured by AUClast and AUC0-∞ as well as the Cmax, Tmax and elimination half-life (t½) for both spinosyns A and D. As the mean doses between treatment groups varied [treatment group 1 (spinosad API in gel capsules to fed animals)=74.3±3.99 mg/kg, treatment group 2 (spinosad tablet to fed animals)=96.1±13.6 mg/kg and treatment group 3 (spinosad tablet to fasted animals)=76.5±11.4 mg/kg], AUC0-∞ and Cmax were normalized to dose.

The spinosyn A and D pharmacokinetic results for Cmax, $t_{1/2}$ and $T_{max}$ as well as $AUC_{last}$ and $AUC_{0-\infty}$ were comparable between treatment groups 1 (80 mg/kg spinosad API in gel capsules to fed animals) and 2 [80 mg/kg spinosad tablets to fed animals]. For example, the mean normalized $AUC_{0-\infty}$ values for spinosyn A (the major factor of spinosad) were comparable at 4,460±1410 hr*ng*kg/mg*mL for group 1 and 4,480±1180 hr*ng*kg/mg*mL for group 2. The mean normalized Cmax values for spinosyn A were comparable at 60±18 and 46±14 ng*kg/mg*mL for treatment groups 1 and 2, respectively. The mean elimination half-lives ($t_{1/2}$) for spinosyn A were comparable at 327±84.3 and 277±75.5 hours for treatment groups 1 and 2, respectively. The mean Tmax values for spinosyn A were comparable at 12±5.2 and 10±3.0 hours for treatment groups 1 and 2, respectively. Spinosyn D values were observed to follow the same trends as spinosyn A. There were no clinically significant sex differences observed in the pharmacokinetic parameters for spinosyns A and D. As the pharmacokinetic results were comparable, it is expected that administration of either spinosad API in gel capsules or spinosad tablets to fed animals would produce similar safety and effectiveness results.

The spinosyn A and D pharmacokinetic results for $t_{1/2}$ and $T_{max}$ in treatment group 3 [80 mg/kg spinosad tablets to fasted animals] were numerically lower than, but comparable to, values from groups 1 and 2. For example, the mean $t_{1/2}$ for spinosyn A was 193±60.5 hours in treatment group 3, compared to 327±84.3 and 277±75.5 hours in treatment groups 1 and 2, respectively. The mean $T_{max}$ was 6.0±3.7 hours in treatment group 3 compared to 12±5.2 and 10±3.0 hours in treatment groups 1 and 2, respectively.

Systemic exposure as measured by $AUC_{0-\infty}$ and $C_{max}$ were substantially greater in fed animals (groups 1 and 2) than in fasted animals (group 3). On average, $AUC_{0-\infty}$ values ranged from 5-10 times greater and Cmax values were 4-7 times higher in fed animals. For example, the mean normalized spinosyn A $AUC_{0-\infty}$ value for treatment group 3 was 781±406 hr*ng*kg/mg*mL, compared to 4,460±1410 and 4,480±1180 hr*ng*kg/mg*mL for treatment groups 1 and 2, respectively. The mean normalized Cmax value was 11±6.6 ng*kg/mg*mL for treatment group 3, compared to 60±18 and 46±14 ng*kg/mg*mL for treatment groups 1 and 2, respectively. Thus, a prandial effect was observed in cats and cats should be in the fed state for maximum absorption of the test article. In conclusion, the pharmacokinetics and biosimilarity of spinosad API (80 mg/kg) and spinosad tablets (80 mg/kg) were comparable following oral administration to cats.

EXAMPLE 3

Dose Confirmation Study to Evaluate Efficacy of a Flavored Spinosad Tablet (Minimum Dose of 50 mg/Kg) Administered Orally to Cats Against Adult Cat Fleas (Ctenocephalides felis)

The treatment effect (insecticidal efficacy) of a beef flavored spinosad tablet when administered orally at a dose of 50-75 mg/kg against fleas (Ctenocephalides felis) on experimentally infested cats can be evaluated at one day post-administration and for the post-treatment prevention effect (residual efficacy) on Days 7, 14, 21 and 28.

In total, twenty-two (22) cats can be acclimatized for the study and from these, 17 can be selected based on pre-treatment weight and flea retention counts to be randomized into either a treated or control group. Nine cats can be assigned to the control group and eight cats can be assigned to the treatment group based on flea retention counts from Day −5. Cats in the treated group can be dosed on Day 0 with the intended final formulation, a beef flavored tablet containing spinosad at a dose rate of 50-75 mg/kg spinosad/body weight, while the cats in the control group can be dosed with a vehicle control tablet.

Each cat can be infested with approximately 100 fleas on Days −1, 7, 14, 21 and 28 and then combed and the fleas counted on Days 1, 9, 16, 23 and 30 respectively.

The spinosad treatment group showed significantly better efficacy (p-value=<0.0001) against adult *C. felis* when compared to the control group at Days 1, 9, 16, 23 and 30. Residual efficacy is calculated on the day of infestation and not on the day the fleas were counted. The percentage efficacy at each study time point is shown in Table 3.

TABLE 3

Geometric Mean Percent Reduction (Geometric Mean Counts) of Adult *C. felis* Compared to Untreated Control Group in Cats Treated Orally with Spinosad

| Spinosad, Oral Dose (mg/kg) | Days Post Treatment | | | | |
|---|---|---|---|---|---|
| | 1 | 7 | 14 | 21 | 28 |
| 50-75 | 100.0 | 100.0 | 99.69 | 99.45 | 98.05 |

Seventeen cats were randomized based on pre-treatment flea infestation counts into either a treated or control group. Eight cats were dosed on Day 0 with a beef flavored tablet containing spinosad with an overall dose range of 51.47 to 76.06 mg/kg spinosad body weight. The other nine cats were dosed with a vehicle control tablet.

Flea counts in the treatment group were significantly reduced (p-value=<0.0001) post-treatment compared to control at all study time points. As shown in Table 3, the percentage efficacy in the spinosad treated group at all study timepoints (Day 1 to Day 28) based on geometric means, demonstrate both the insecticidal and residual efficacy of spinosad at a minimum dose of 50 mg/kg. All 17 cats completed the study and adequately tolerated the spinosad.

In conclusion, this example demonstrates that the flavored spinosad tablet given orally at a dose of 50-75 mg/kg significantly reduced flea counts at one day post-treatment and for a period of at least 28 days post-treatment.

EXAMPLE 4

Dose Confirmation Study to Evaluate Efficacy of a Flavored Spinosad Tablet (Minimum Dose of 50 mg/Kg) Administered Orally to Cats Against Adult Cat Fleas (*Ctenocephalides felis*)

Confirmation of the efficacious dose of spinosad can be evaluated in cats experimentally infested with adult fleas (*Ctenocephalides felis*).

Twenty-four (24) cats that meet the inclusion/exclusion criteria and had the highest pre-treatment live flea (*C. felis*) counts can be included in a randomized complete block design with pre-treatment live flea counts used as a blocking factor. Each cat can be infested with approximately 100 unfed adult fleas (*C. felis*) on Test Day −9. Pre-treatment live flea counts can be conducted using the laboratory's comb counting method on Test Day −7. The Test Day −7 live flea counts can be used to allocate cats to one of two treatment groups. The two treatment groups of 12 cats per group can be orally dosed on Test Day 0. One group (5 male: 7 female) can receive vehicle control (0 mg/kg placebo tablets) and the second group (7 male: 5 female) can receive flavored spinosad tablets at a dose rate of 50-75 mg/kg body weight. Cats can consume canned cat food just prior to dosing and can be offered their daily maintenance diet after dosing. Each cat can be infested with approximately 100 unfed adult fleas (*C. felis*) on Test Days −1, 5, 12, 19, 28 and 35. Individual animal live flea counts can be performed on Test Days 1, 7, 14, 21, 30 and 37. Efficacy against experimentally induced adult *C. felis* populations can be determined by comparing post-treatment flea counts from the treated and vehicle control groups.

The pre-treatment geometric mean (GM) flea count was 70.1 (range 59-86) in the vehicle control group and 70.5 (range 60-99) in the spinosad treated group. The control group GM ranged between 63.7 and 74.3 on post-treatment count days. The level of infestation was adequate in both groups pre-treatment and comparable between the groups prior to treatment based on WAAVP Guidelines (2007). Retention remained high in the vehicle control group post-treatment.

Spinosad provided 100% knockdown on Study Day 1. The residual efficacy based on geometric means was 99.78%, 99.57%, 95.83%, 90.77% and 90.36% for Days 7, 14, 21, 30 and 37, respectively. The difference between the control and spinosad groups was significant on all study days (Days 1, 7, 14, 21, 30 and 37; p<0.0001 on each day).

This example indicates the effectiveness of spinosad against adult *C. felis* was confirmed at the lower half of the unit dosage range for oral administration to cats as a flavored tablet. In summary, flavored spinosad tablets administered orally to cats (50-75 mg/kg spinosad) were both safe and efficacious (based on geometric means) delivering excellent knockdown (100% on Day 1 post-treatment) and residual (90.77% at Day 30 post-treatment) adult flea control on experimentally infested cats evaluated under laboratory conditions. In addition, 50-75 mg/kg of flavored spinosad tablets administered orally to cats demonstrated 90.36% residual efficacy at Day 37 post-treatment.

The invention claimed is:

1. A single-dose oral formulation for controlling a *C. felis* infestation on a cat comprising an ectoparasiticidal amount of spinosad, microcrystalline cellulose, hydroxypropylcellulose, colloidal silicon (anhydrous), croscarmellose sodium, and magnesium stearate, and optionally an artificial flavor, wherein the formulation is suitable for oral administration once every 30 days at a dose of at least about 50 mg of spinosad per kg of body weight of the cat, wherein the formulation comprises the following weight/weight percentages:

| | |
|---|---|
| Pharmaceutical grade spinosad (API) | 53.33% |
| Microcrystalline cellulose, NF/Ph. Eur. | 14.17% |
| Hydroxypropyl cellulose, NF/Ph. Eur. | 5.0% |
| Croscarmellose sodium, NF/Ph. Eur. | 6.0% |
| Colloidal silicon dioxide, NF/Ph. Eur. | 0.5% |
| Magnesium stearate, NF/Ph. Eur. (non-bovine) | 1.0% |
| Purified Water, USP/Ph. Eur | q.s. |

2. A single-dose oral formulation for controlling a *C. felis* infestation on a cat comprising an ectoparasiticidal amount of spinosad, microcrystalline cellulose, hydroxypropylcellulose, colloidal silicon (anhydrous), croscarmellose sodium, and magnesium stearate, and optionally an artificial flavor, wherein the formulation is suitable for oral administration once every 30 days at a dose of at least about 50 mg of spinosad per kg of body weight of the cat, wherein the formulation comprises the following weight/weight percentages:

| | |
|---|---|
| Pharmaceutical grade spinosad (API) | 53.33% |
| Artificial powdered beef flavor PC-0125 (gamma irradiated) | 20.00% |
| Microcrystalline cellulose, NF/Ph. Eur. | 14.17% |
| Hydroxypropyl cellulose, NF/Ph. Eur. | 5.0% |
| Croscarmellose sodium, NF/Ph. Eur. | 6.0% |
| Colloidal silicon dioxide, NF/Ph. Eur. | 0.5% |
| Magnesium stearate, NF/Ph. Eur. (non-bovine) | 1.0% |
| Purified Water, USP/Ph. Eur | q.s. |

3. The formulation of claim 1, wherein the formulation has greater than 75% residual efficacy at 30 days post-administration.

4. The formulation of claim 1, wherein the formulation has greater than 90% residual efficacy at 30 days post-administration.

5. The formulation of claim 1, wherein the formulation has greater than 95% residual efficacy at 30 days post-administration.

6. The formulation of claim 1, wherein the formulation is a tablet or capsule.

7. A method of controlling a *C. felis* infestation on a cat, the method comprising orally administering to the cat a single-dose oral formulation comprising an ectoparasiticidal amount of spinosad, microcrystalline cellulose, hydroxypropylcellulose, colloidal silicon (anhydrous), croscarmellose sodium, and magnesium stearate, and optionally an artificial flavor, wherein the formulation is suitable for oral administration once every 30 days at a dose of at least about 50 mg of spinosad per kg of body weight of the cat, and wherein the formulation comprises the following weight/weight percentages:

| | |
|---|---|
| Pharmaceutical grade spinosad (API) | 53.33% |
| Microcrystalline cellulose, NF/Ph. Eur. | 14.17% |
| Hydroxypropyl cellulose, NF/Ph. Eur. | 5.0% |
| Croscarmellose sodium, NF/Ph. Eur. | 6.0% |
| Colloidal silicon dioxide, NF/Ph. Eur. | 0.5% |
| Magnesium stearate, NF/Ph. Eur. (non-bovine) | 1.0% |
| Purified Water, USP/Ph. Eur | q.s. |

8. The method of claim 7, wherein the dose is at least about 75 mg of spinosad per kg of body weight of the cat.

9. The method of claim 7, wherein the dose is at least about 100 mg of spinosad per kg of body weight of the cat.

10. The method of claim 7, wherein the formulation comprises the following weight/weight percentages:

| | |
|---|---|
| Pharmaceutical grade spinosad (API) | 53.33% |
| Artificial powdered beef flavor PC-0125 (gamma irradiated) | 20.00% |
| Microcrystalline cellulose, NF/Ph. Eur. | 14.17% |
| Hydroxypropyl cellulose, NF/Ph. Eur. | 5.0% |
| Croscarmellose sodium, NF/Ph. Eur. | 6.0% |
| Colloidal silicon dioxide, NF/Ph. Eur. | 0.5% |
| Magnesium stearate, NF/Ph. Eur. (non-bovine) | 1.0% |
| Purified Water, USP/Ph. Eur | q.s. |

11. The method of claim 7, wherein the formulation has greater than 75% residual efficacy at 30 days post-administration.

12. The method of claim 7, wherein the formulation has greater than 90% residual efficacy at 30 days post-administration.

13. The method of claim 7, wherein the formulation has greater than 95% residual efficacy at 30 days post-administration.

14. The method of claim 7, wherein the formulation is a tablet or capsule.

15. A single-dose oral tablet for controlling a *C. felis* infestation on a cat comprising spinosad, microcrystalline cellulose, artificial beef flavor, hydroxypropylcellulose, colloidal silicon (anhydrous), croscarmellose sodium, and magnesium stearate, wherein the spinosad is present in an amount of at least about 90 mg, wherein the tablet is suitable for oral administration once every 30 days, and wherein the tablet comprises the following amounts:

| | |
|---|---|
| Pharmaceutical grade spinosad (API) | 90 mg |
| Artificial powdered beef flavor PC-0125 (gamma irradiated) | 33.75 mg |
| Microcrystalline cellulose, NF/Ph. Eur. | 23.91 mg |
| Hydroxypropyl cellulose, NF/Ph. Eur. | 8.44 mg |
| Croscarmellose sodium, NF/Ph. Eur. | 10.13 mg |
| Colloidal silicon dioxide, NF/Ph. Eur. | 0.84 mg |
| Magnesium stearate, NF/Ph. Eur. (non-bovine) | 1.69 mg |
| Purified Water, USP/Ph. Eur | q.s. |

16. A single-dose oral tablet for controlling a *C. felis* infestation on a cat comprising spinosad, microcrystalline cellulose, artificial beef flavor, hydroxypropylcellulose, colloidal silicon (anhydrous), croscarmellose sodium, and magnesium stearate, wherein the spinosad is present in an amount of at least about 140 mg, wherein the tablet is suitable for oral administration once every 30 days, and wherein the tablet comprises the following amounts:

| | |
|---|---|
| Pharmaceutical grade spinosad (API) | 140 mg |
| Artificial powdered beef flavor PC-0125 (gamma irradiated) | 52.50 mg |
| Microcrystalline cellulose, NF/Ph. Eur. | 37.20 mg |
| Hydroxypropyl cellulose, NF/Ph. Eur. | 13.13 mg |
| Croscarmellose sodium, NF/Ph. Eur. | 15.75 mg |
| Colloidal silicon dioxide, NF/Ph. Eur. | 1.31 mg |
| Magnesium stearate, NF/Ph. Eur. (non-bovine) | 2.63 mg |
| Purified Water, USP/Ph. Eur | q.s. |

17. A single-dose oral tablet for controlling a *C. felis* infestation on a cat comprising spinosad, microcrystalline cellulose, artificial beef flavor, hydroxypropylcellulose, colloidal silicon (anhydrous), croscarmellose sodium, and magnesium stearate, wherein the spinosad is present in an amount of at least about 270 mg, wherein the tablet is suitable for oral administration once every 30 days, and wherein the tablet comprises the following amounts:

| | |
|---|---|
| Pharmaceutical grade spinosad (API) | 270 mg |
| Artificial powdered beef flavor PC-0125 (gamma irradiated) | 101.26 mg |
| Microcrystalline cellulose, NF/Ph. Eur. | 71.74 mg |
| Hydroxypropyl cellulose, NF/Ph. Eur. | 25.31 mg |
| Croscarmellose sodium, NF/Ph. Eur. | 30.38 mg |
| Colloidal silicon dioxide, NF/Ph. Eur. | 2.53 mg |
| Magnesium stearate, NF/Ph. Eur. (non-bovine) | 5.06 mg |
| Purified Water, USP/Ph. Eur | q.s. |

18. A single-dose oral tablet for controlling a *C. felis* infestation on a cat comprising spinosad, microcrystalline cellulose, artificial beef flavor, hydroxypropylcellulose, colloidal silicon (anhydrous), croscarmellose sodium, and magnesium stearate, wherein the spinosad is present in an amount of at least about 560 mg, wherein the tablet is suitable for oral administration once every 30 days, and wherein the tablet comprises the following amounts:

| | |
|---|---|
| Pharmaceutical grade spinosad (API) | 560 mg |
| Artificial powdered beef flavor PC-0125 (gamma irradiated) | 210 mg |
| Microcrystalline cellulose, NF/Ph. Eur. | 148.8 mg |
| Hydroxypropyl cellulose, NF/Ph. Eur. | 52.52 mg |
| Croscarmellose sodium, NF/Ph. Eur. | 63 mg |
| Colloidal silicon dioxide, NF/Ph. Eur. | 5.24 mg |
| Magnesium stearate, NF/Ph. Eur. (non-bovine) | 10.52 mg |
| Purified Water, USP/Ph. Eur | q.s. |

19. The tablet of claim 15, wherein the tablet has greater than 75% residual efficacy at 30 days post-administration.

20. The tablet of claim 15, wherein the tablet has greater than 90% residual efficacy at 30 days post-administration.

21. The tablet of claim 15, wherein the tablet has greater than 95% residual efficacy at 30 days post-administration.

22. The formulation of claim 2, wherein the formulation has greater than 75% residual efficacy at 30 days post-administration.

23. The formulation of claim 2, wherein the formulation has greater than 90% residual efficacy at 30 days post-administration.

24. The formulation of claim 2, wherein the formulation has greater than 95% residual efficacy at 30 days post-administration.

25. The formulation of claim 2, wherein the formulation is a tablet or capsule.

26. The tablet of claim 16, wherein the tablet has greater than 75% residual efficacy at 30 days post-administration.

27. The tablet of claim 16, wherein the tablet has greater than 90% residual efficacy at 30 days post-administration.

28. The tablet of claim 16, wherein the tablet has greater than 95% residual efficacy at 30 days post-administration.

29. The tablet of claim 17, wherein the tablet has greater than 75% residual efficacy at 30 days post-administration.

30. The tablet of claim 17, wherein the tablet has greater than 90% residual efficacy at 30 days post-administration.

31. The tablet of claim 17, wherein the tablet has greater than 95% residual efficacy at 30 days post-administration.

32. The tablet of claim 18, wherein the tablet has greater than 75% residual efficacy at 30 days post-administration.

33. The tablet of claim 18, wherein the tablet has greater than 90% residual efficacy at 30 days post-administration.

34. The tablet of claim 18, wherein the tablet has greater than 95% residual efficacy at 30 days post-administration.

\* \* \* \* \*